(12) United States Patent
Volkmann et al.

(10) Patent No.: US 10,072,018 B2
(45) Date of Patent: *Sep. 11, 2018

(54) COMPOUNDS FOR TREATMENT OF PAIN

(71) Applicant: BioPharma Works, Groton, CT (US)

(72) Inventors: Robert Volkmann, Mystic, CT (US); Anthony Marfat, Old Lyme, CT (US); Peter Cornelius, Old Lyme, CT (US); Panayiotis Zagouras, Old Saybrook, CT (US); Fredrick Raymond Nelson, Groton, CT (US); Anton Franz Joseph Fliri, Stonington, CT (US)

(73) Assignee: BIOPHARMA WORKS, Groton, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/785,545

(22) PCT Filed: Apr. 16, 2014

(86) PCT No.: PCT/US2014/034398
§ 371 (c)(1),
(2) Date: Oct. 19, 2015

(87) PCT Pub. No.: WO2014/172478
PCT Pub. Date: Oct. 23, 2014

(65) Prior Publication Data
US 2016/0083393 A1   Mar. 24, 2016

Related U.S. Application Data

(60) Provisional application No. 61/813,143, filed on Apr. 17, 2013.

(51) Int. Cl.
| C07D 471/00 | (2006.01) |
| C07D 491/00 | (2006.01) |
| C07D 498/00 | (2006.01) |
| C07D 513/00 | (2006.01) |
| C07D 515/00 | (2006.01) |
| C07D 489/04 | (2006.01) |
| A01N 43/42 | (2006.01) |
| A61K 31/44 | (2006.01) |

(52) U.S. Cl.
CPC .................. C07D 489/04 (2013.01)

(58) Field of Classification Search
None
See application file for complete search history.

(56) References Cited

U.S. PATENT DOCUMENTS

| 4,277,489 A | 7/1981 | Vandoni | |
| 2007/0060500 A1* | 3/2007 | Mickle | A61K 9/0019 514/21.6 |
| 2008/0188423 A1 | 8/2008 | Garlich et al. | |
| 2008/0318905 A1* | 12/2008 | Muhammad | A61K 47/48084 514/81 |
| 2011/0040072 A1* | 2/2011 | Mickle | A61K 9/0019 530/330 |
| 2011/0178068 A1* | 7/2011 | Almarsson | A61K 31/343 514/220 |
| 2012/0077811 A1 | 3/2012 | Smaill et al. | |

FOREIGN PATENT DOCUMENTS

| WO | 0137785 A2 | 5/2001 |
| WO | 2008070149 A2 | 6/2008 |
| WO | 2008101202 A1 | 8/2008 |
| WO | 2014172482 A1 | 10/2014 |

OTHER PUBLICATIONS

Davidsen et al. 'N-(Acyloxyalkyl)pyridinium Salts as Soluble Prodrugs of a Potent Platelet Activating Fact or Antagonist', J.Med. Chem., Dec. 23, 1994, vol. 37, No. 26, pp. 4423-4429. Abstract; p. 4425 Table 1.

Krise et al. 'A Novel Prodrug Approach for Tertiary Amines. 2. Physicochemical and in Vitro Enzymatic Evaluation of Selected N-Phosphonooxymethyl Prodrugs', Published in Journal of Pharmaceutical Sciences vol. 88, No. 9, Sep. 1999, 6 pages.

Krise et al. 'Novel Prodrug Approach for Tertiary Amines: Synthesis and Preliminary Evaluation N-Phosphonoxymethyl Prodrugs' Published in Journal of Medicinal Chemistry, 1999, vol. 42, No. 16, 7 pages.

Krise et al. 'A Novel Prodrug Approach for Tertiary Amines. 3. in Vivo Evaluation of Two N-Phosphonooxymethyl Prodrugs in Rats and Dogs' Published in Journal of Pharmaceutical Sciences vol. 88, No. 9, Sep. 1999, 5 pages.

Nielson et al. 'Bioreversible quaternary N-acyloxymethyl derivatives of the poorly soluble tertiary amine Lu 28-179-Synthsis, pharmaceutical chemical characterization and bioavailability studies in dogs' Published in European Journal of Pharmaceutical Sciences 26 (2005) 421-428, 8 pages.

Search Report from the International Searching Authority for International application No. PCT/US14/34398, filed Apr. 16, 2014, 13 pages.

Extended European Search Report, Application No. 14785169.5-1462/2986294 PCT/US2014/034398, dated Oct. 14, 2016, 7 pages.

* cited by examiner

*Primary Examiner* — Daniel Michael Podgorski
(74) *Attorney, Agent, or Firm* — Ziegler IP Law Group, LLC

(57) ABSTRACT

The aspects of the disclosed embodiments are directed to novel compounds, specifically, quaternary ammonium derivatives of tertiary amine containing opioid drug compounds such as hydrocodone, hydromorphone and oxycodone, formulations containing said. compounds or pharmaceutically acceptable salts thereof, which are capable of providing controlled release of the opioid drug upon administration to a patient in order to treat pain.

3 Claims, No Drawings

COMPOUNDS FOR TREATMENT OF PAIN

FIELD

The aspects of the disclosed embodiments are directed to novel compounds, formulations containing said compounds or pharmaceutically acceptable salts thereof which are suitable for administration to a patient.

BACKGROUND

This disclosure is directed to quaternary oxycodone, oxymorphone, hydrocodone and hydromorphone ammonium compounds described in general Formula I and to compositions and uses of said compounds for treating pain associated with a variety of chronic human disorders including for example neuropathic pain and pain associated with cancer, surgeries or injuries.

The compounds of the disclosure may be generically categorized within the class of compounds known as opioids. It is well known that opioid drugs target three types of endogenous opioid receptors (i.e., mu, delta and kappa receptors) in biological systems. Most opioids, such as morphine, are mu opioid agonists that are often used as analgesics for the treatment of severe pain due to their activation of mu opioid receptors in the brain and central nervous system (CNS). Opioid receptors are, however, not limited to the CNS, and have been found in other tissues throughout the body. A number of side effects of opioid drugs may be caused by activation of these peripheral receptors including nausea, vomiting and inhibition of normal propulsive gastrointestinal function resulting in side effects such as, for example, constipation, drowsiness, respiratory depression, changes in mood, and mental clouding without a resulting loss of consciousness. Thus, it is widely recognized that opioid treatment induced constipation is sometimes even more difficult to treat than the underlying pain. Towards this end, several ameliorating strategies have been developed which include, for example, the administration of opioid receptor antagonist such as for example, Naltrexon to patients for reversing opioid induced constipation. However, since central acting opioid receptor antagonists also reverse analgesia and precipitate opioid withdrawal symptoms, non CNS penetrant quaternary ammonium derivatives of opioid antagonist such as for example, Methyl Naltrexone have been developed and these derivatives have been shown to reverse peripheral side effects of opioids without inducing CNS mediated withdrawal symptoms or reversing analgesia. However, since use of opioid antagonists targets the amelioration of already manifested side effects, these treatment regimens add cost and burden to the treatment of pain. Accordingly there is a need for developing opioid derivatives that would exhibit reduced peripheral side-effects while maintaining central analgesic properties.

Moreover, prescription opioid use is also the subject of extensive "substance abuse" which is increasing and exacts a high toll on patients, physicians, and society. Nonmedical users of prescription pain relievers quadrupled from 1990 to 2000, with abuse of oxycodone and hydrocodone products particularly common. Extracting a societal toll, this prescription drug abuse is associated with higher rates of comorbidities and drug-related mortality.

Chronic pain and prescription opioid abuse are both highly prevalent. Chronic pain affects approximately 50 million Americans each year, and an additional 48 million Americans 12 years or older have used prescription drugs for nonmedical reasons in their lifetimes. Among the most potent analgesics available, opioids have a recognized role in the treatment of cancer- and non-cancer-related chronic pain conditions. Yet many physicians, concerned that their patients will become addicted, are reluctant to prescribe these agents, contributing to the widespread undertreatment of chronic pain.

One strategy for reducing the potential for abuse is development of tamper resistant opioid formulations designed to create barriers to manipulations of prescription drug formulations. Additionally, opioid formulations incorporating pharmacological strategies have also been designed to deter or resist misuse and abuse by making it difficult to achieve euphoria through opioid use. As pharmacologically proactive tools, these formulations use either pharmacodynamic or physical mechanisms to make opioids unattractive to individuals who abuse them, as well as present barriers to unintentional or deliberate misuse. Such formulations are currently available and have had mixed epidemiological results. New compounds and formulations that obviate the limitations of existing therapeutics are thus needed.

Pharmaceutical strategies have been developed as either agonist-antagonist or agonist-additional active ingredient combinations. Agonist-antagonist formulations can be considered pharmacodynamic strategies because they act to reduce reward at the receptor level. An example of such a strategy is Embeda™ (Pfizer™) which combines morphine with an antagonist such as naltrexone. If this formulation is ingested normally, the naltrexone remains latent; if it is crushed, the naltrexone is released and reduces the effects of the morphine Other agonist-antagonist combinations include Talwin™ containing pentazocine hydrochloride and naloxone hydrochloride equivalent; Valoron™, a combination of tilidine and naloxone; and Terngesic, a combination of buprenorphine and naloxone. These strategies cause, in some instances, opioid withdrawal symptoms.

Opioids with a reduced side effect and abuse potential are one of the most important unmet needs in the management of chronic pain and help physicians to better balance optimal analgesia with reduced risk of having to treat either opioid induced side effects or worry about prescription misuse and abuse.

Compounds of the present disclosure combine agonist/antagonist activity at opioid receptors in a single molecular entity and exploit (as principle of their pharmacological action) relative drug distribution/partitioning differences between agonist and quaternary ammonium antagonist in peripheral and central nervous system compartments, thereby reducing peripheral side effects associated with opioid receptor agonist use (such as GI effects, or respiratory depression and pruritis). In addition, by controlling the delivery of a centrally acting analgesic opioid through the rate of enzymatic conversion of a peripheral quaternary ammonium opioid antagonist, compounds of the present invention are abuse-resistant while maintaining analgesic properties of the parent opioid.

The invention relates to a compound of Formula I:

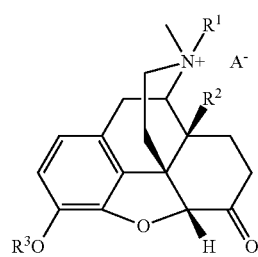

wherein $R^1$ is $CHR^4O(C=O)OR^5$, $CHR^4O(C=O)R^6$, $CHR^4O(C=O)NR^6R^7$, $CHR^4O(C=O)CHR^8NR^6R^7$, $CHR^4O(C=O)CHR^8NH(COCHR^8NH)_nH$, $CHR^4R^9$, $CHR^4O(C=O)CR^5R^6OR^7$, $CHR^4O(C=O)O(CH_2)_n NR^5R^6$, $CHR^4O(C=O)O(CH_2)_nCO_2R^5$, $CHR^4O(C=O) (CH_2)_nNR^5R^6$, $CHR^4O(C=O)(CH_2)_nCO_2R^5$,

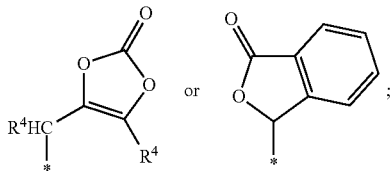

$R^2$ is H, OH, or $O(C=O)CH_3$;
$R^3$ is H, $CH_3$, or $(C=O)CH_3$;
$R^4$ is H or optionally substituted alkyl; wherein said substituents are independently selected from the group $OR^3$ and $(C=O)OR^5$;
$R^5$ is optionally substituted alkyl, cycloalkyl, phenylalkyl, heteroalkyl, heterocycloalkyl, aryl, or heteroaryl; wherein said substituents are independently $(CH_2)_nCO_2$alkyl;
$R^6$ is H or $R^5$;
$R^7$ is H or $R^5$;
$R^8$ is H or $R^5$;
$R^9$ is 4-isoxazoyl;
wherein n is an integer from 1-12; and
A is an anion selected from the group consisting of: $Br^-$, $Cl^-$, $I^-$, $R^7CO_2^-$, $H_2PO_4^-$, $NO_3^-$, Etodolate, Mefenamate, Urosodeoxycholate and $R^6SO_3$.

Alkyl means unsubstituted and substituted, straight-chain and branched-chain alkyls having from 1 to 20 carbon atoms; alkyl may also contain one or multiple numbers of unsaturation including double and/or triple bonds; straight chain alkyl includes methyl, ethyl, propyl, butyl group, pentyl (to be also referred to as an amyl group) hexyl, decyl), branched chain alkyl group includes isopropyl, diethylmethyl, isobutyl, sec-butyl, t-butyl, isopentyl, t-pentyl, 2-ethylhexyl and the like; alkyl is also optionally substituted with 1 or more substituents independently selected from the group consisting of halo, hydroxy, alkoxy(alkoxy)x, hydroxyalkoxy(alkoxy)x, amino, monoalkylamino, dialkylamino, nitro, carboxyl, alkoxycarbonyl, and cyano, wherein x is an integer from 0 to 3 and the alkoxy contains from 1 to 5 carbon atoms.

Cycloalkyl means cyclopropyl, cyclobutyl, cyclopentyl and cyclohexyl; and said cyclic alkyl is optionally substituted with 1 or 2 substituents independently selected from the group consisting of halo, hydroxy, alkoxy(alkoxy)x, hydroxyalkoxy(alkoxy)x, amino, monoalkylamino, dialkylamino, nitro, carboxyl, alkoxycarbonyl, and cyano, wherein x is an integer from 0 to 3 and the alkoxy portion of the alkoxycarbonyl contains from 1 to 5 carbon atoms.

Phenylalkyl is selected from the group consisting of benzyl, phenylethyl and phenylpropyl; and the phenyl portion of the phenylalkyl is optionally substituted with 1 to 3 substituents independently selected from the group consisting of alkyl, hydroxy, alkoxy, halo, amino, monoalkylamino, dialkylamino, nitro, carboxyl, alkoxycarbonyl and cyano, wherein the phenyl portion of the phenylalkyl is unsubstituted or substituted.

Heteroalkyl means a straight or branched-chain having from one to 20 carbon atoms and one or more heteroatoms selected from nitrogen, oxygen, or sulphur, wherein the nitrogen and sulphur atoms may optionally be oxidized, i.e., in the form of an N-oxide or an S-oxide.

Heterocycloalkyl means a monocyclic or multicyclic ring system (which may be saturated or partially unsaturated), including fused and spiro rings, of about five to about 10 elements wherein one or more of the elements in the ring system is an element other than carbon and is selected from nitrogen, oxygen, silicon, or sulphur atoms.

Aryl means phenyl or napthyl wherein the phenyl or napthyl moiety is optionally substituted with 1 to 3 substituents independently selected from the group consisting of alkyl, hydroxy, alkoxy, halo, amino, monoalkylamino, dialkylamino, nitro, carboxyl, alkoxycarbonyl and cyano groups.

Heteroaryl means a five to about a 14-membered aromatic monocyclic or multicyclic hydrocarbon ring system, including fused and spiro rings, in which one or more of the elements in the ring system is an element other than carbon and is selected from nitrogen, oxygen, silicon, or sulphur and wherein an N atom may be in the form of an N-oxide.

Natural, synthetic, racemic, L-, or D-amino acid group as used herein refers to a substituent containing 1 to 20 amino acid. When two or more amino acids are linked together the group is known as a polypeptide. The polypeptide may be (i) an oligopeptide, (ii) a homopolymer of one of the twenty naturally occurring amino acids, (iii) a heteropolymer of two or more naturally occurring amino acids, (iv) a homopolymer of a synthetic amino acid, (v) a heteropolymer of two or more synthetic amino acids or (vi) a heteropolymer of one or more naturally occurring amino acids and one or more synthetic amino acids. Polypeptides include the twenty naturally occurring amino acids. Specific polypeptides include one or more amino acids selected from glutamic acid, aspartic acid, arginine, asparagine, cysteine, lysine, threonine, or serine. Such peptides may be attached through the C-terminus or the N-terminus.

Selection of the particular amino acids will depend on the physical properties desired. For instance, properties such as bulk, lipophilicity, and hydrophilicity may be optimized according to selection parameters known to those skilled in the art.

Sugar or saccharide as used herein refers to a monosaccharide, a disaccharide, polysaccharide or sugar alcohol. Saccharide includes galactose, fructose, glucose, maltose, cellobiose, gentiobiose, melibiose, lactose, turanose, sophorose, trehalose, isotrehalose, isosaccharose, white sugar, mannitol, sorbitol, xylitol or inositol.

Compounds of Formula I exist in the form of quaternary ammonium cations ionically complexed with pharmaceutically acceptable anions derived from acids to form addition salts of the compounds of Formula I. The phrase "pharmaceutically acceptable salt(s)", as used herein, unless otherwise indicated, includes salts of quaternary ammonium compounds of Formula I.

Suitable salts are formed from acids which form non-toxic salts and may include acids that are known to enhance the pharmacologic utility of opioids. Examples include the acetate, adipate, aspartate, benzoate, besylate, bicarbonate/carbonate, bisulphate/sulphate, borate, camsylate, chenodeoxycholate, citrate, cyclamate, edisylate, Etodolate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mefenamate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, salycilate, saccharate, stearate, succinate, tannate, tartrate, tosylate, trifluoroacetate, Ursodexoycholate and xinofoate salts. Suitable anions include $Br^-$, $Cl^-$, $I^-$, $R^7CO_2^-$, $H_2PO_4^-$, $NO_3^-$, and $R^6SO_3$. Hemisalts may also be formed, for example, hemisulphate. For a review on suitable salts, see *Handbook of Pharmaceutical Salts: Properties, Selection, and Use* by Stahl and Wermuth (Wiley-VCH, 2002).

As used herein the term "Formula I" is defined to include all forms of the compounds of Formula I, including hydrates, solvates, isomers, crystalline and non-crystalline forms, isomorphs, polymorphs, and metabolites thereof.

The compounds of the present disclosure may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order (Melting point').

The compounds of the present disclosure may also exist in unsolvated and solvated forms. The term 'solvate' is used herein to describe a molecular complex comprising the compound according to the present disclosure and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the aspects of the disclosed embodiments are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see *Chem Commun*, 17, 1889-1896, by O. Almarsson and M. J. Zaworotko (2004). For a general review of multi-component complexes, see *J Pharm Sci*, 64 (8), 1269-1288, by Haleblian (August 1975).

The compounds according to the disclosed embodiments may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $-COO^-Na^+$, $-COO^-K^+$, or $-SO_3^-Na^+$) or non-ionic (such as $-N^-N^+(CH_3)_3$) polar head group. For more information, see *Crystals and the Polarizing Microscope* by N. H. Hartshorne and A. Stuart, 4$^{th}$ Edition (Edward Arnold, 1970).

Hereinafter all references to compounds of Formula I include references to salts, solvates, multi-component complexes and liquid crystals thereof and to solvates, multi-component complexes and liquid crystals of salts thereof.

The compounds of the present disclosure include compounds of Formula I as hereinbefore defined, including all polymorphs and crystal habits thereof, and isomers thereof (including optical, geometric and tautomeric isomers) as hereinafter defined and isotopically-labeled compounds of Formula I.

The compounds of Formula I have asymmetric carbon and nitrogen atoms and exist as two or more stereoisomers. The bonds of the compounds of Formula I may be depicted herein using a solid line (—), a solid wedge (——), or a dotted wedge (........). The use of a solid line to depict bonds to asymmetric carbon atoms is meant to indicate that all possible stereoisomers (e.g. specific enantiomers, racemic mixtures, etc.) at that atom are included. The use of either a solid or dotted wedge to depict bonds to asymmetric atoms is meant to indicate that only the stereoisomer shown is meant to be included. It is possible that compounds of Formula I may contain more than one asymmetric atom. In those compounds, the use of a solid line to depict bonds to asymmetric atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric atoms in a compound of Formula I and the use of a solid or dotted wedge to depict bonds to other asymmetric atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of Formula I, including compounds exhibiting more than one type of isomerism; and mixtures thereof (such as racemates and diastereomeric pairs).

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the Formula I may exhibit the phenomena of tautomerism and structural isomerism. For example, the compounds of Formula I may exist in several tautomeric forms, including the enol and imine form, and the keto and enamine form and geometric isomers and mixtures thereof. All such tautomeric forms are included within the scope of compounds of Formula I. Tautomers exist as mixtures of a tautomeric set in solution. In solid form, usually one tautomer predominates. Even though one tautomer may be described, the disclosed embodiments include all tautomers of the compounds of Formula I.

The present invention includes all pharmaceutically acceptable isotopically-labelled compounds of Formula I wherein one or more atoms are replaced by atoms having the same atomic number, but an atomic mass or mass number different from the atomic mass or mass number which predominates in nature.

Examples of isotopes suitable for inclusion in the compounds of the present disclosure include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of Formula I, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of Formula I can generally be prepared by conventional techniques known to those skilled in the art or by processes analogous to those described in the accompanying Examples and Preparations using an appropriate isotopically-labeled reagent in place of the non-labeled reagent previously employed.

Another embodiment relates to compounds of Formula I, wherein the stereochemistry about the quaternary nitrogen center is in the "S" configuration.

Another embodiment relates to compounds of Formula I, wherein the stereochemistry about the quaternary nitrogen center is in the "R" configuration.

Compounds of Formula I of particular interest can be segregated according to established opioid skeletons (wherein $R^2$ and $R^3$ groups have been replaced) as described below:

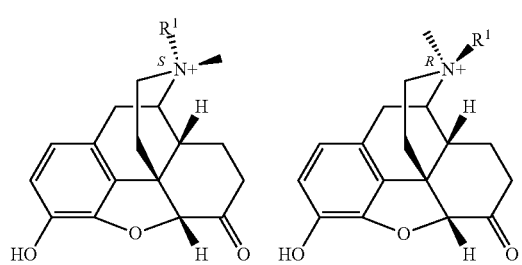

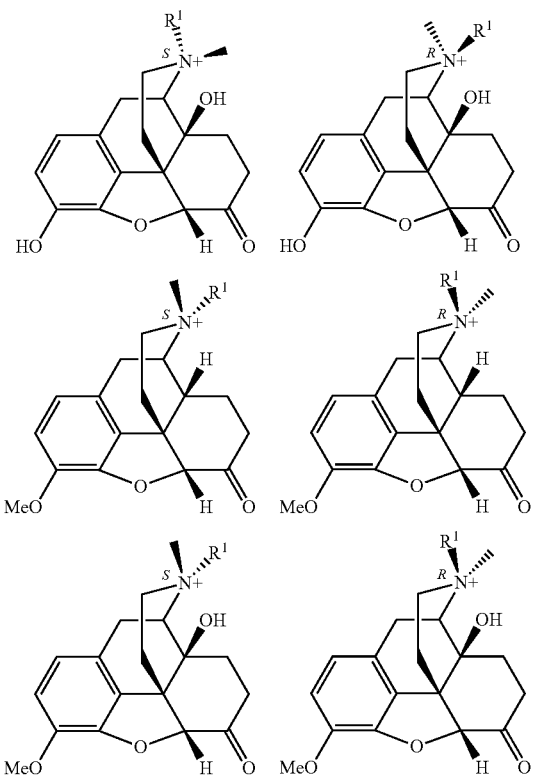

Another embodiment of the present disclosure refers to compounds of Formula I wherein the $R^1$ groups (taken together with the $R^4$, $R^5$ and $R^6$ functionality) have the formulae:

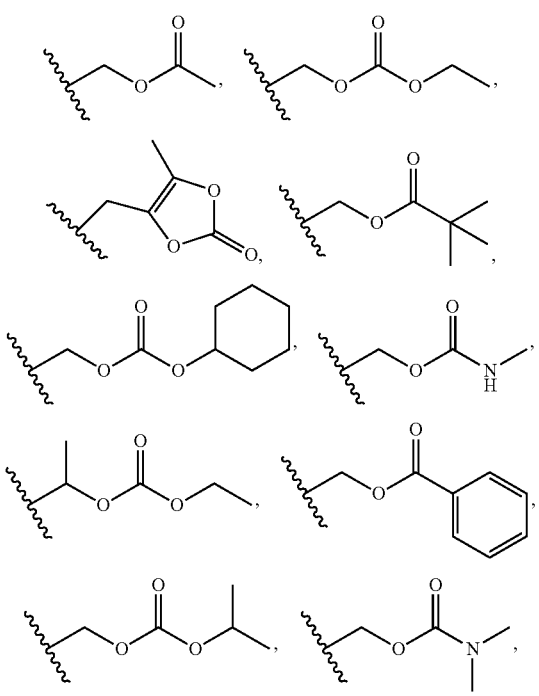

-continued

[chemical structures: ester with OEt group, and isobutyrate ester]

Another embodiment relates to compounds of Formula I, wherein $R^1$ is $CHR^4O(C=O)OR^5$.

Another embodiment relates to compounds of Formula I, wherein $R^1$ is $CHR^4O(C=O)R^6$.

Another embodiment relates to compounds of Formula I, wherein $R^1$ is $CHR^4O(C=O)NR^6R^7$.

Another embodiment relates to compounds of Formula I, wherein $R^1$ is $CHR^4O(C=O)CHR^8NR^6R^7$.

Another embodiment relates to compounds of Formula I, wherein $R^1$ is $CHR^4O(C=O)CHR^8NH(COCHR^8NH)_nH$.

Another embodiment relates to compounds of Formula I, wherein $R^1$ is $CHR^4R^9$.

Another embodiment relates to compounds of Formula I, wherein $R^1$ is $CHR^4O(C=O)CR^5R^6OR^7$.

Another embodiment relates to compounds of Formula I, wherein $R^1$ is $CHR^4O(C=O)O(CH_2)_nNR^5R^6$.

Another embodiment relates to compounds of Formula I, wherein $R^1$ is $CHR^4O(C=O)O(CH_2)_nCO_2R^5$.

Another embodiment relates to compounds of Formula I, wherein $R^1$ is $CHR^4O(C=O)(CH_2)_nNR^5R^6$.

Another embodiment relates to compounds of Formula I, wherein $R^1$ is $CHR^4O(C=O)(CH_2)_nCO_2R^5$.

Another embodiment relates to compounds of Formula I, wherein $R^1$ is

[chemical structure: dioxolenone with $R^4HC$ and $R^4$ substituents]

Another embodiment relates to compounds of Formula I, wherein $R^1$ is

[chemical structure: phthalide/isobenzofuranone]

Another embodiment relates to compounds of Formula I, wherein $R^2$ is H. Other embodiments relate to compounds of Formula I, wherein $R^2$ is H and $R^1$ is one of the aforesaid embodiments relating to $R^1$.

Another embodiment relates to compounds of Formula I, wherein $R^2$ is OH. Other embodiments relate to compounds of Formula I, wherein $R^2$ is OH and $R^1$ is one of the aforesaid embodiments relating to $R^1$.

Another embodiment relates to compounds of Formula I, wherein $R^2$ is $O(C=O)CH_3$. Other embodiments relate to compounds of Formula I, wherein $R^2$ is $O(C=O)CH_3$ and $R^1$ is one of the aforesaid embodiments relating to $R^1$.

Another embodiment relates to compounds of Formula I, wherein $R^3$ is H. Other embodiments relate to compounds of Formula I, wherein $R^3$ is H and $R^1$ is one of the aforesaid embodiments relating to $R^1$. Other embodiments relate to compounds of Formula I, wherein $R^3$ is H and $R^1$ is one of the aforesaid embodiments relating to $R^1$ and/or $R^2$ is one of the aforesaid embodiments relating to $R^2$.

Another embodiment relates to compounds of Formula I, wherein $R^3$ is Methyl. Other embodiments relate to compounds of Formula I, wherein $R^3$ is methyl and $R^1$ is one of the aforesaid embodiments relating to $R^1$. Other embodiments relate to compounds of Formula I, wherein $R^3$ is methyl and $R^1$ is one of the aforesaid embodiments relating to $R^1$ and/or $R^2$ is one of the aforesaid embodiments relating to $R^2$.

Another embodiment relates to compounds of Formula I, wherein $R^3$ is $(C=O)CH_3$. Other embodiments relate to compounds of Formula I, wherein $R^3$ is $(C=O)CH_3$ and $R^1$ is one of the aforesaid embodiments relating to $R^1$. Other embodiments relate to compounds of Formula I, wherein $R^3$ is $(C=O)CH_3$ and $R^1$ is one of the aforesaid embodiments relating to $R^1$ and/or $R^2$ is one of the aforesaid embodiments relating to $R^2$.

Another embodiment relates to compounds of Formula I, wherein $R^4$ is H. Other embodiments relate to compounds of Formula I, wherein $R^4$ is H and $R^1$ is one of the aforesaid embodiments relating to $R^1$. Other embodiments relate to compounds of Formula I, wherein $R^4$ is H and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$.

Another embodiment relates to compounds of Formula I, wherein $R^4$ is methyl, ethyl, isopropyl, t-butyl, diethylmethyl, or pentyl. Other embodiments relate to compounds of Formula I, wherein $R^4$ is methyl, ethyl, isopropyl, t-butyl, diethylmethyl, or pentyl and $R^1$ is one of the aforesaid embodiments relating to $R^1$. Other embodiments relate to compounds of Formula I, wherein $R^4$ is methyl, ethyl, isopropyl, t-butyl, diethylmethyl, or pentyl and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$.

Another embodiment relates to compounds of Formula I, wherein $R^4$ is alkyl optionally substituted with one or more substituents independently selected from the group $OR^3$ and $(C=O)OR^5$. Other embodiments relate to compounds of Formula I, wherein $R^4$ is alkyl optionally substituted with one or more substituents independently selected from the group $OR^3$ and $(C=O)OR^5$ and $R^1$ is one of the aforesaid embodiments relating to $R^1$. Other embodiments relate to compounds of Formula I, wherein $R^4$ is alkyl optionally substituted with one or more substituents independently selected from the group $OR^3$ and $(C=O)OR^5$ and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$.

Another embodiment relates to compounds of Formula I, wherein $R^5$ is alkyl selected from methyl, ethyl, isopropyl, n-butyl, or n-pentyl. Other embodiments relate to compounds of Formula I, wherein $R^5$ is alkyl selected from methyl, ethyl, isopropyl, n-butyl, or n-pentyl and $R^1$ is one of the aforesaid embodiments relating to $R^1$. Other embodiments relate to compounds of Formula I, wherein $R^5$ is alkyl selected from methyl, ethyl, isopropyl, n-butyl, or n-pentyl and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$ and/or $R^4$ is one of the aforesaid embodiments relating to $R^4$.

Another embodiment relates to compounds of Formula I, wherein $R^5$ is optionally substituted alkyl, wherein said substituent(s) is $(CH_2)_nCO_2$alkyl; and wherein n is an integer from 1-12. Other embodiments relate to compounds of Formula I, wherein $R^5$ is optionally substituted alkyl, wherein said substituent(s) is $(CH_2)_nCO_2$alkyl; and wherein n is an integer from 1-12 and $R^1$ is one of the aforesaid embodiments relating to $R^1$. Other embodiments relate to compounds of Formula I, wherein $R^5$ is optionally substituted alkyl, wherein said substituent(s) is $(CH_2)_nCO_2$alkyl; and wherein n is an integer from 1-12 and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$ and/or $R^4$ is one of the aforesaid embodiments relating to $R^4$.

Another embodiment relates to compounds of Formula I, wherein $R^5$ is cyclohexyl. Other embodiments relate to compounds of Formula I, wherein $R^5$ is cyclohexyl and $R^1$ is one of the aforesaid embodiments relating to $R^1$. Other embodiments relate to compounds of Formula I, $R^5$ is cyclohexyl and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$ and/or $R^4$ is one of the aforesaid embodiments relating to $R^4$.

Another embodiment relates to compounds of Formula I, wherein $R^5$ is benzyl. Other embodiments relate to compounds of Formula I, wherein $R^5$ is benzyl and $R^1$ is one of the aforesaid embodiments relating to $R^1$. Other embodiments relate to compounds of Formula I, $R^5$ is benzyl and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$ and/or $R^4$ is one of the aforesaid embodiments relating to $R^4$.

Another embodiment relates to compounds of Formula I, wherein $R^6$ is H. Other embodiments relate to compounds of Formula I, wherein $R^6$ is H and $R^1$ is one of the aforesaid embodiments relating to $R^1$. Other embodiments relate to compounds of Formula I, wherein $R^6$ is H and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$ and/or $R^4$ is one of the aforesaid embodiments relating to $R^4$.

Another embodiment relates to compounds of Formula I, wherein $R^6$ is methyl. Other embodiments relate to compounds of Formula I, wherein $R^6$ is methyl and $R^1$ is one of the aforesaid embodiments relating to $R^1$. Other embodiments relate to compounds of Formula I, $R^6$ is methyl and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$ and/or $R^4$ is one of the aforesaid embodiments relating to $R^4$.

Another embodiment relates to compounds of Formula I, wherein $R^6$ is t-butyl. Other embodiments relate to compounds of Formula I, wherein $R^6$ is t-butyl and $R^1$ is one of the aforesaid embodiments relating to $R^1$. Other embodiments relate to compounds of Formula I, wherein $R^6$ is t-butyl and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$ and/or $R^4$ is one of the aforesaid embodiments relating to $R^4$.

Another embodiment relates to compounds of Formula I, wherein $R^6$ is i-propyl. Other embodiments relate to compounds of Formula I, wherein $R^6$ is i-propyl and $R^1$ is one of the aforesaid embodiments relating to $R^1$. Other embodiments relate to compounds of Formula I, $R^6$ is i-propyl and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$ and/or $R^4$ is one of the aforesaid embodiments relating to $R^4$.

Another embodiment relates to compounds of Formula I, wherein $R^6$ is cyclohexyl. Other embodiments relate to compounds of Formula I, wherein $R^6$ is cyclohexyl and $R^1$ is one of the aforesaid embodiments relating to $R^1$. Other embodiments relate to compounds of Formula I, wherein $R^6$ is cyclohexyl and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$ and/or $R^4$ is one of the aforesaid embodiments relating to $R^4$.

Another embodiment relates to compounds of Formula I, wherein $R^6$ is benzyl. Other embodiments relate to compounds of Formula I, wherein $R^6$ is benzyl and $R^1$ is one of the aforesaid embodiments relating to $R^1$. Other embodiments relate to compounds of Formula I, $R^6$ is benzyl and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$ and/or $R^4$ is one of the aforesaid embodiments relating to $R^4$.

Another embodiment relates to compounds of Formula I, wherein $R^6$ is phenyl. Other embodiments relate to compounds of Formula I, wherein $R^6$ is phenyl and $R^1$ is one of the aforesaid embodiments relating to $R^1$. Other embodiments relate to compounds of Formula I, wherein $R^6$ is phenyl and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$ and/or $R^4$ is one of the aforesaid embodiments relating to $R^4$.

Another embodiment relates to compounds of Formula I, wherein $R^7$ is H. Other embodiments relate to compounds of Formula I, wherein $R^7$ is H and $R^1$ is one of the aforesaid embodiments relating to $R^1$. Other embodiments relate to compounds of Formula I, wherein $R^7$ is H and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$ and/or $R^4$ is one of the aforesaid embodiments relating to $R^4$.

Another embodiment relates to compounds of Formula I, wherein $R^7$ is methyl. Other embodiments relate to compounds of Formula I, wherein $R^7$ is methyl and $R^1$ is one of the aforesaid embodiments relating to $R^1$. Other embodiments relate to compounds of Formula I, wherein $R^7$ is methyl and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$ and/or $R^4$ is one of the aforesaid embodiments relating to $R^4$.

Another embodiment relates to compounds of Formula I, wherein $R^6$ is H. Other embodiments relate to compounds of Formula I, wherein $R^8$ is H and $R^1$ is one of the aforesaid embodiments relating to $R^1$. Other embodiments relate to compounds of Formula I, wherein $R^8$ is H and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$ and/or $R^4$ is one of the aforesaid embodiments relating to $R^4$.

Another embodiment relates to compounds of Formula I, wherein $R^8$ is methyl. Other embodiments relate to compounds of Formula I, wherein $R^8$ is methyl and $R^1$ is one of the aforesaid embodiments relating to $R^1$. Other embodiments relate to compounds of Formula I, wherein $R^8$ is methyl and/or $R^1$ is one of the aforesaid embodiments relating to $R^1$ and/or $R^2$ is one of the aforesaid embodiments relating to $R^2$ and/or $R^3$ is one of the aforesaid embodiments relating to $R^3$ and/or $R^4$ is one of the aforesaid embodiments relating to $R^4$.

Another embodiment relates to compounds of Formula I, wherein $R^9$ is 4-isoxazoyl. Other embodiments relate to said $R^9$ 4-isoxazoyl embodiments taken in combination with the $R^1$, $R^2$, $R^3$, $R^4$ and/or $R^5$ embodiments described herein above.

Another embodiment relates to compounds of Formula I, wherein A is $Br^-$. Other embodiments relate to said A as $Br^-$ embodiments taken in combination with the other $R^1$, $R^2$, $R^3$, $R^4$ and/or $R^5$ embodiments described herein above.

Another embodiment relates to compounds of Formula I, wherein A is $Cl^-$. Other embodiments relate to said A is $Cl^-$ embodiments taken in combination with the other $R^1$, $R^2$, $R^3$, $R^4$ and/or $R^5$ embodiments described herein above.

Another embodiment relates to compounds of Formula I, wherein A is $I^-$. Other embodiments relate to said A is $I^-$ embodiments taken in combination with the other $R^1$, $R^2$, $R^3$, $R^4$ and/or $R^5$ embodiments described herein above.

Another embodiment relates to compounds of Formula I, wherein A is $R^7CO_2^-$, more specifically lactate, acetate, tartrate, and valerate. Other embodiments relate to said A is $R^7CO_2^-$ embodiments taken in combination with the other $R^1$, $R^2$, $R^3$, $R^4$ and/or $R^5$ embodiments. described herein above.

Another embodiment relates to compounds of Formula I, wherein A is $H_2PO_4^-$. Other embodiments relate to said A as $H_2PO_4^-$ embodiments taken in combination with the other $R^1$, $R^2$, $R^3$, $R^4$ and/or $R^5$ embodiments described herein above.

Another embodiment relates to compounds of Formula I, wherein A is $NO_3^-$. Other embodiments relate to said A as $NO_3^-$ embodiments taken in combination with the other $R^1$, $R^2$, $R^3$, $R^4$ and/or $R^5$ embodiments described herein above.

Another embodiment relates to compounds of Formula I, wherein A is $R^6SO_3$. Other embodiments relate to said A as $R^6SO_3$ embodiments taken in combination with the other $R^1$, $R^2$, $R^3$, $R^4$ and/or $R^5$ embodiments described herein above.

Another embodiment relates to compounds of Formula I, wherein A is Ursodeoxycholate. Other embodiments relate to said A as Ursodeoxycholate embodiments taken in combination with the other $R^1$, $R^2$, $R^3$, $R^4$ and/or $R^5$ embodiments described herein above.

Another embodiment relates to compounds of Formula I, wherein A is Etodolate. Other embodiments relate to said A as Etodolate embodiments taken in combination with the other $R^1$, $R^2$, $R^3$, $R^4$ and/or $R^5$ embodiments described herein above.

Another embodiment relates to compounds of Formula I, wherein A is Mefanamate. Other embodiments relate to said A as Mefanamate embodiments taken in combination with the other $R^1$, $R^2$, $R^3$, $R^4$ and/or $R^5$ embodiments described herein above.

Another embodiment of the invention relates to the following specific compounds of the invention:

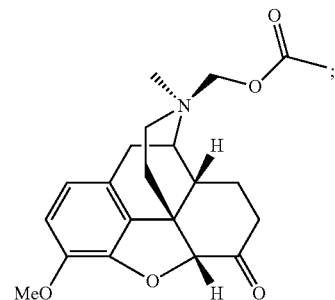

((3R,4aR,7aR,12bS)-9-methoxy-3-methyl-7-oxo-1,2,4,4a,5,6,7,7a-octahydro-3H-3λ⁴-4,12-methanobenzofuro[3,2-e]isoquinolin-3-yl)methyl acetate

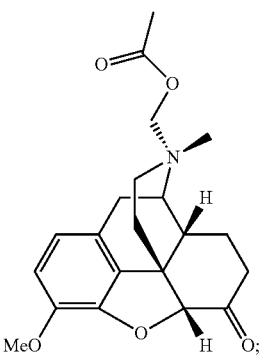

((3S,4aR,7aR,12bS)-9-methoxy-3-methyl-7-oxo-1,2,4,4a,5,6,7,7a-octahydro-3H-3l⁴-4,12-methanobenzofuro[3,2-e]isoquinolin-3-yl)methyl acetate

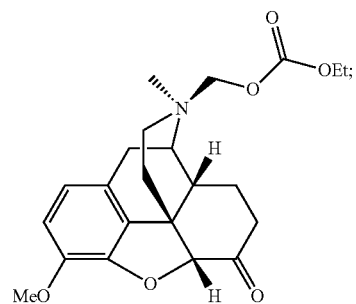

ethyl (((3R,4aR,7aR,12bS)-9-methoxy-3-methyl-7-oxo-1,2,4,4a,5,6,7,7a-octahydro-3H-3l⁴-4,12-methanobenzofuro[3,2-e]isoquinolin-3-yl)methyl) carbonate

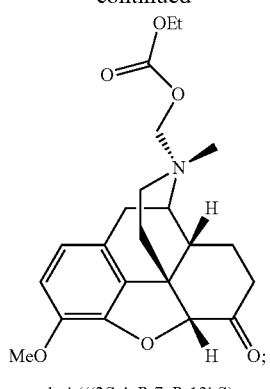

ethyl (((3S,4aR,7aR,12bS)-
9-methoxy-3-methyl-7-oxo-
1,2,4,4a,5,6,7,7a-octahydro-
3H-3I⁴-4,12-methanobenzofuro
[3,2-e]isoquinolin-3-yl]methyl)
carbonate

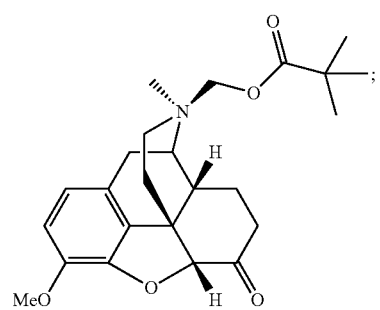

((3R,4aR,7aR,12bS)-9-methoxy-3-
methyl-7-oxo-1,2,4,4a,5,6,7,7a-
octahydro-3H-3λ⁴-4,12-
methanobenzofuro[3,2-e]isoquinolin-
3-yl)methyl pivalate

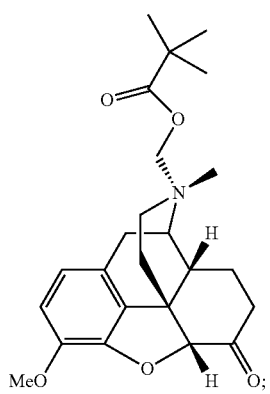

((3S,4aR,7aR,12bS)-
9-methoxy-3-
methyl-7-oxo-1,2,4,4a,5,6,7,7a-
octahydro-3H-3λ⁴-4,12-
methanobenzofuro[3,2-
e]isoquinolin-3-yl)methyl
pivalate

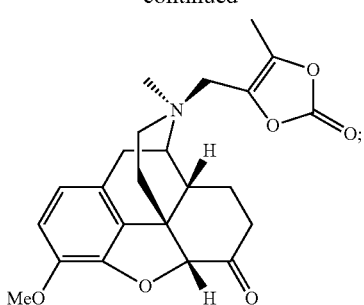

(3S,4aR,7aR,12bS)-9-methoxy-3-
methyl-3-((5-methyl-2-oxo-
1,3-dioxol-4-yl)methyl)-
2,3,4,4a,5,6-hexahydro-1H-3λ⁴-4,12-
methanobenzofuro[3,2-e]isoquinolin-
7(7aH)-one

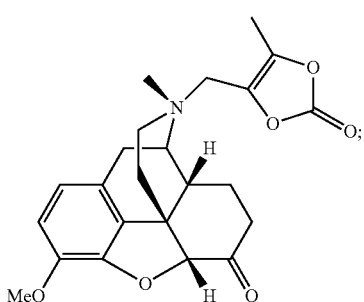

(3R,4aR,7aR,12bS)-9-methoxy-3-
methyl-3-((5-methyl-2-oxo-
1,3-dioxol-4-yl)methyl)-
2,3,4,4a,5,6-hexahydro-1H-3λ⁴-4,12-
methanobenzofuro[3,2-e]isoquinolin-
7(7aH)-one

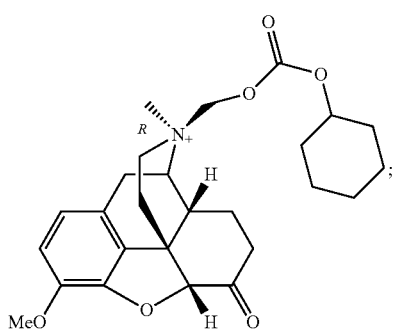

(3R,4aR,7aR,12bS)-3-
(((((cyclohexyloxy)carbonyl)oxy)methyl)-9-methoxy-
3-methyl-7-oxo-2,3,4,4a,5,6,7,7a-octahydro-1H-
4,12-methanobenzofuro[3,2-e]isoquinolin-3-ium -continued

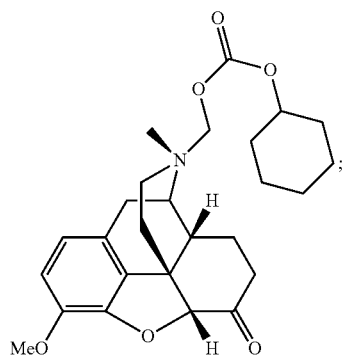

cyclohexyl (((3S,4aR,7aR,12bS)-9-
methoxy-3-methyl-7-oxo-
1,2,4,4a,5,6,7,7a-octahydro-3H-
3λ⁴-4,12-methanobenzofuro[3,2-
e]isoquinolin-3-yl)methyl) carbonate

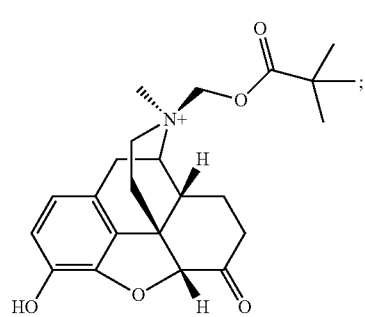

(3R,4aR,7aR,12bS)-9-hydroxy-3-methyl-7-
oxo-3-((pivaloyloxy)methyl)-
2,3,4,4a,5,6,7,7a-octahydro-1H-4,12-
methanobenzofuro[3,2-e]isoquinolin-3-ium

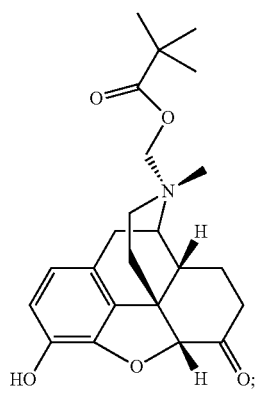

((3S,4aR,7aR,12bS)-
9-hydroxy-3-
methyl-7-oxo-1,2,4,4a,5,6,7,7a-
octahydro-3H-3λ⁴-4,12-
methanobenzofuro[3,2-
e]isoquinolin-3-yl)methyl
pivalate -continued

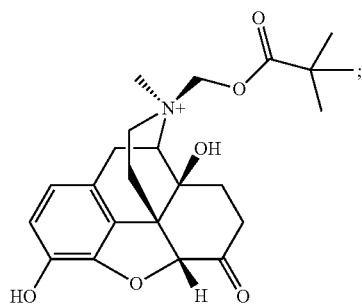

(3R,4aS,7aR,12bS)-4a,9-dihydroxy-3-methyl-
7-oxo-3-((pivaloyloxy)methyl)-
2,3,4,4a,5,6,7,7a-octahydro-1H-4,12-
methanobenzofuro[3,2-e]isoquinolin-3-ium

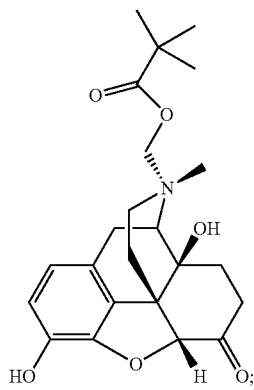

((3S,4aS,7aR,12bS)-
4a,9-dihydroxy-3-
methyl-7-oxo-1,2,4,4a,5,6,7,7a-
octahydro-3H-3λ⁴-4,12-
methanobenzofuro[3,2-
e]isoquinolin-3-yl)methyl
pivalate

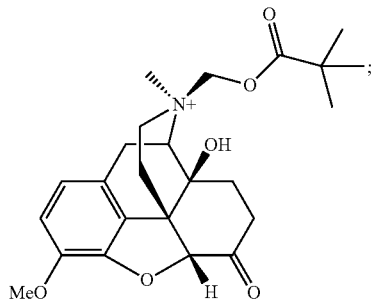

(3R,4aS,7aR,12bS)-4a-hydroxy-9-methoxy-
3-methyl-7-oxo-3-((pivaloyloxy)methyl)-
2,3,4,4a,5,6,7,7a-octahydro-1H-4,12-
methanobenzofuro[3,2-e]isoquinolin-3-ium

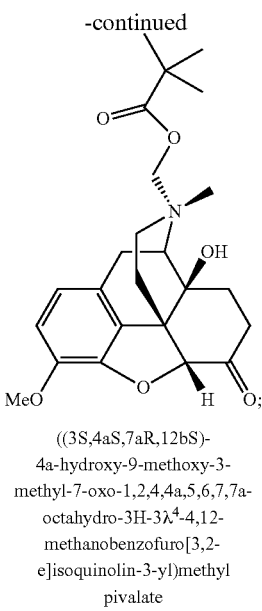

((3S,4aS,7aR,12bS)-
4a-hydroxy-9-methoxy-3-
methyl-7-oxo-1,2,4,4a,5,6,7,7a-
octahydro-3H-3λ$^4$-4,12-
methanobenzofuro[3,2-
e]isoquinolin-3-yl)methyl
pivalate The compounds of Formula I (and the other embodiments above) are useful in the treatment of pain, particularly neuropathic, nociceptive and inflammatory pain.

Another embodiment relates to a method of treating acute or chronic pain comprising administering to a patient an effective amount of a compound of Formula I.

The aspects of the disclosed embodiments also relate to compositions comprising a compound of Formula I. Accordingly one embodiment relates to a pharmaceutical composition comprising a pharmaceutically effective amount of a compound of Formula I, a pharmaceutically acceptable carrier and, optionally, at least one additional medicinal or pharmaceutical agent.

Another embodiment relates to a composition of any of the aforesaid embodiments of compounds of Formula I wherein said composition is in tablet, capsule, oral solution, or oral suspension dosage form.

Another embodiment relates to a composition of a compound of Formula I wherein said composition is in tablet or capsule dosage form.

Another embodiment relates to an oral pharmaceutical preparation containing a therapeutically effective amount of a compound of Formula I for once daily administration.

Another embodiment relates to a sustained release composition containing a compound of Formula I.

In yet further embodiments, the pharmaceutical composition in addition to the compound of Formula I may further include a non-opioid drug. Such non-opioid drugs would preferably provide additional analgesia, and include, for example, aspirin; acetaminophen; non-steroidal anti-inflammatory drugs ("NSAIDS"), e.g., ibuprofen, ketoprofen, etc.; N-methyl-D-aspartate (NMDA) receptor antagonists, e.g., a morphinan such as dextromethorphan or dextrorphan, or ketamine; cyclooxygenase-II inhibitors ("COX-II inhibitors"); and/or glycine receptor antagonists.

Suitable non-steroidal anti-inflammatory agents, include ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, pharmaceutically acceptable salts thereof, mixtures thereof, and the like. Useful dosages of these drugs are well known to those skilled in the art.

N-methyl-D-aspartate (NMDA) receptor antagonists are well known in the art, and encompass, for example, morphinans such as dextromethorphan or dextrorphan, ketamine, or pharmaceutically acceptable salts thereof. For purposes of the present disclosure, the term "NMDA antagonist" is also deemed to encompass drugs that at least partially inhibit a major intracellular consequence of NMDA-receptor activation, e.g. a ganglioside such as GM.sub.1 or GT.sub.1b, a phenothiazine such as trifluoperazine or a naphthalenesulfonamide such as N-(6-aminothexyl)-5-chloro-1-naphthalenesulfonamide. These drugs are stated to inhibit the development of tolerance to and/or dependence on addictive drugs, e.g., narcotic analgesics such as morphine, codeine, etc. in U.S. Pat. Nos. 5,321,012 and 5,556,838 (both to Mayer, et al.), and to treat chronic pain in U.S. Pat. No. 5,502,058 (Mayer, et al.). The NMDA antagonist may be included alone, or in combination with a local anesthetic such as lidocaine, as described in these Mayer, et al. patents.

The treatment of chronic pain via the use of glycine receptor antagonists and the identification of such drugs is described in U.S. Pat. No. 5,514,680 (Weber, et al.).

COX-2 inhibitors have been reported in the art and many chemical structures are known to produce inhibition of cyclooxygenase-2. COX-2 inhibitors are described, for example, in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311. Certain preferred COX-2 inhibitors include celecoxib, flosulide, meloxicam, 6-methoxy-2 naphthylacetic acid (6-MNA), nabumetone (prodrug for 6-MNA), nimesulide, or combinations thereof. Dosage levels of COX-2 inhibitor on the order of from about 0.005 mg to about 140 mg per kilogram of body weight per day are therapeutically effective in combination with the compounds of Formula I. Alternatively, about 0.25 mg to about 7 g per patient per day of a COX-2 inhibitor is administered in a combination.

In yet further embodiments, a non-opioid drug can be included which provides a desired effect other than analgesia, e.g., antitussive, expectorant, decongestant, antihistamine drugs, local anesthetics, and the like.

The pharmaceutically acceptable carrier may comprise any conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Physiological pain is an important protective mechanism designed to warn of danger from potentially injurious stimuli from the external environment. The system operates through a specific set of primary sensory neurons and is activated by noxious stimuli via peripheral transducing mechanisms (see Millan, 1999, Prog. Neurobiol., 57, 1-164 for a review). These sensory fibers are known as nociceptors and are characteristically small diameter axons with slow conduction velocities. Nociceptors encode the intensity, duration and quality of noxious stimulus and by virtue of their topographically organized projection to the spinal cord, the location of the stimulus. The nociceptors are found on nociceptive nerve fibers of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, post herpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitization in the periphery, locally around the injury and centrally where the nociceptors terminate. These effects lead to a heightened sensation of pain. In acute pain these mechanisms can be useful, in promoting protective behaviors which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibers associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibers. Myelinated A-delta fibers transmit rapidly and are responsible for sharp and stabbing pain sensations, whilst unmyelinated C fibers transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), posttraumatic pain, renal colic, cancer pain and back pain. Cancer pain may be chronic pain such as tumor related pain (e.g. bone pain, headache, facial pain or visceral pain) or pain associated with cancer therapy (e.g. post chemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse etiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact etiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge &

Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple etiologies and thus can be classified in more than one area, e.g. back pain and cancer pain have both nociceptive and neuropathic components.

Other types of pain include: pain resulting from muscular-skeletal disorders, including myalgia, fibromyalgia, spondylitis, sero-negative (non-rheumatoid) arthropathies, non-articular rheumatism, dystrophinopathy, glycogenolysis, polymyositis and pyomyositis; heart and vascular pain, including pain caused by angina, myocardical infarction, mitral stenosis, pericarditis, Raynaud's phenomenon, scleredoma and skeletal muscle ischemia; head pain, such as migraine (including migraine with aura and migraine without aura), cluster headache, tension-type headache mixed headache and headache associated with vascular disorders; erythermalgia; and orofacial pain, including dental pain, otic pain, burning mouth syndrome and temporomandibular myofascial pain.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

Administration of the compounds of Formula I may be effected by any method that enables delivery of the compounds to the site of action. These methods include oral routes, intraduodenal routes, parenteral injection (including intravenous, subcutaneous, intramuscular, intravascular or infusion), topical, and rectal administration.

The aspects of the disclosed embodiments also relate to altering the pharmacokinetic and pharmacological properties of opioids, particularly oxycodone, oxymorphone, hydrocodone and hydromorphone, through quaternization of the bicyclic tertiary amine embedded in the opioid structure. It is well known to those skilled in the art that quaternization can change the rate and extent of absorption, metabolism, distribution, and elimination of a drug. Moreover, preferred quaternary ammonium compounds of the present disclosure possess opioid antagonist activity. Furthermore, the quaternary ammonium compounds of the disclosure, when ingested or administered to a patient by any other means, are converted to free base opioid possessing agonist activity at opioid receptors. Thus, these compounds inherently possess both antagonist and agonist properties. When the quaternary ammonium compound is first orally administered it may bind to opioid receptors. More specifically, if a quaternary ammonium compound of the disclosure is orally ingested, the compound upon reaching the intestinal tract binds to the mu or delta opioid receptor acting as an antagonist. Simultaneously, quaternary ammonium opioid compound is subject to the action of intestinal metabolic action and uptake and further metabolism by intestinal wall transmission processes. These processes are responsible for converting the quaternary ammonium opioid into the tertiary amine parent compound (i.e. oxycodone, oxymorphone and hydromorphone). Although the opioid is now free to act in the intestinal tract as an agonist the receptors have already been blocked by prior saturation with the antagonistic quaternary compound. This localized inactivation of opioid receptors reduces local side effects such as constipation, a major side effect of agonists. When administered at a normal therapeutic dose the bioavailablility (the time-versus-concentration curve; area under the curve; AUC) of the opioid may be similar to that observed with slow or extended release formulations of the parent free base opioid compound. However, since the uptake (systemic bioavailability) of the quaternary ammonium opioid derivative into the circulation is generally much lower when compared with the uptake of the parent opioid compounds, this differential uptake property causes a relative decline of the parent opioid agonist concentration in intestinal compartments and maintains the potential of the antagonist to reduce agonist induced constipation. In contrast, the parent opioid agonist derived from the quaternary ammonium precursor through the action of metabolic enzymes is readily taken up into the circulation, enters the central nervous system where it exerts its analgesic activity. Moreover, the quaternary ammonium antagonist is restricted from crossing the blood brain barrier and thus has negligible penetration into the central nervous system. Furthermore, since means for generating euphoria aim at very rapid delivery of relatively large amounts of an opioid into the central nervous system; compounds embraced in general formula 1 are abuse resistant because enzymes control the amounts of opioid available for CNS uptake and the speed of release from a quaternary ammonium precursor cannot be altered even if compounds are taken above doses intended in the prescription or in deviation of the recommended route of administration. Likewise, the active principal in opioid abuse cannot be easily obtained from quaternary ammonium precursors adding a second barrier to drug abuse. This in turn diminishes the abuse potential, whether unintended or intentionally sought.

Persons that abuse opioids such as hydrocodone or oxycodone commonly seek to increase their euphoria by snorting or injecting the drugs. These routes of administration increase the rate and extent of drug absorption and provide a faster, nearly instantaneous, effect. This increases the amount of drug that reaches the central nervous system where it has its effect. In a particular aspect of the disclosed embodiments, the bioavailability of the covalently modified opioid is substantially decreased by the intranasal and intravenous routes as compared to the parent opioid compound. Thus the illicit practice of snorting and shooting the drug loses its advantage.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the aspects of the disclosed embodiments.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the aspects of the disclosed embodiments encompass intra-patient dose-escalation as determined by the skilled artisan. Determining appropriate dosages and regimens for administration of the active agent are well-known in the relevant art and would be understood to be encompassed by the skilled artisan once provided the teachings disclosed herein.

The amount of the compound of Formula I administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

As used herein, the term "combination therapy" refers to the administration of a compound of Formula I together with an at least one additional pharmaceutical or medicinal agent, either sequentially or simultaneously.

The aspects of the disclosed embodiments include the use of a combination of a compound as provided in Formula I and one or more additional pharmaceutically active agent(s). If a combination of active agents is administered, then they may be administered sequentially or simultaneously, in separate dosage forms or combined in a single dosage form. Accordingly, the present disclosure also includes pharmaceutical compositions comprising an amount of: (a) a first agent comprising a compound of Formula I; (b) a second pharmaceutically active agent; and (c) a pharmaceutically acceptable carrier, vehicle or diluent.

Various pharmaceutically active agents may be selected for use in conjunction with the compounds of Formula I, depending on the disease, disorder, or condition to be treated.

DETAILED DESCRIPTION

In the reaction schemes and Formulae that follow $R^1$ through $R^9$, n, and A are as defined above.

Scheme 1

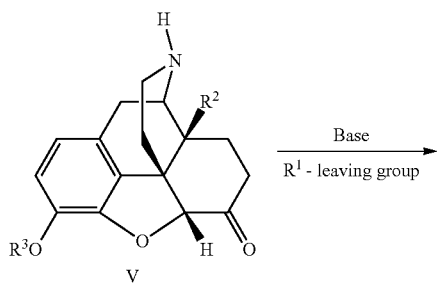

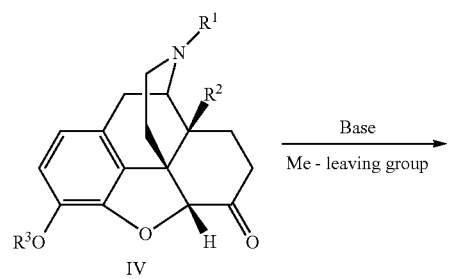

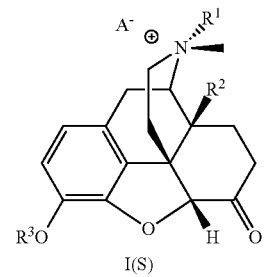

Scheme 2

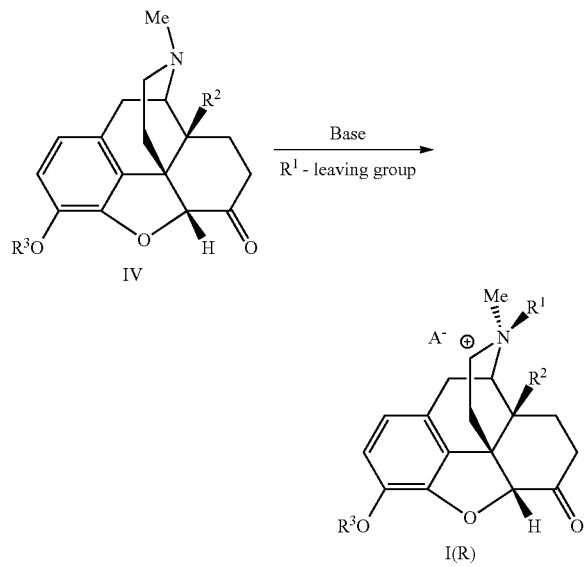

Compounds of the Formula I may be subcategorized into recognized individual opioid skeletons including oxycodone, hydrocodone, oxymorphone and hydromorphone as described above. Each of these skeletons is associated with copious synthetic methods well known to those skilled in the art. Thus starting materials of the Formula IV and V are commercially available or can be made by methods well known to those skilled in the art. See for example U.S. Pat. No. 8,183,376, U.S. Pat. Nos. 2,628,962, 2,654,756 and 2,649,454 (hydromorphone and others); U.S. Pat. No. 2,715,626 (hydrocodone and others); U.S. Pat. No. 2,806,033 (oxymorphone and others); Freund et al. (1916) J. Prak. Chemie 94:135-178 (oxycodone).

In general the compounds of the disclosed embodiments may be made by processes which include processes analogous to those known in the chemical arts, particularly in light of the description contained herein. The compounds of the disclosed embodiments also have asymmetric nitrogen atoms and exist as two stereoisomers around the quaternary ammonium nitrogen. Other asymmetric carbon atoms exist in these compounds enlarging the number of possible stereoisomers.

Scheme 1 refers to the preparation of compounds of Formula I having the "S" stereochemistry about the quaternary ammonium nitrogen. Referring to Scheme 1, compounds of Formula IV may be produced by reaction of free base des-methyl opioid of Formula V, such as Norhydromorphone, Noroxymorphone, Noroxycodone, Norhydrocodone, with a halomethyl acetate, carbonate, carbamate, or isoxazolylate, such as chloromethyl acetate, in the presence of a strong base, such as for example, NaH, LDA and KO$^t$Bu.

The alpha methyl acetate, carbonate, carbamate, or isoxazolylate (including derivatives of Formula II or III when using appropriate activated reagents) compound of Formula IV may be reacted with a methylating agent such as methyl iodide in the presence of a base to form the "S" enantiomeric quaternary ammonium compound of Formula I.

Scheme 2 refers to the preparation of compounds of Formula I having the "R" stereochemistry about the quaternary ammonium nitrogen. Referring to Scheme 2, free base opioid compounds of Formula IV may be reacted with a halomethyl acetate, carbonate, carbamate, or isoxazolylate, such as chloromethyl acetate, in the presence of a strong base such as for example, NaH, LDA, KO$^t$Bu to form a compound of Formula I.

As an initial note, in the preparation of the Formula I compounds it is noted that some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, Protective Groups in Organic Synthesis, John Wiley & Sons, New York, 1991.

Compounds of Formula I that have chiral centers may exist as stereoisomers, such as racemates, enantiomers, or diastereomers. Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of Formula I (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomeric conglomerates may be separated by conventional techniques known to those skilled in the art. See, e.g. "Stereochemistry of Organic Compounds" by E. L. Eliel (Wiley, New York, 1994), the disclosure of which is incorporated herein by reference in its entirety.

Where a compound of Formula I contains an alkenyl or alkenylene group, geometric cis/trans (or Z/E) isomers are possible. Cis/trans isomers may be separated by conventional techniques well known to those skilled in the art, for example, chromatography and fractional crystallization. Salts of the present disclosure can be prepared according to methods known to those of skill in the art.

Polymorphs can be prepared according to techniques well-known to those skilled in the art.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Chiral compounds of the disclosed embodiments (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, Stereochemistry of Organic Compounds by E. L. Eliel and S. H. Wilen (Wiley, 1994).

The aspects of the disclosed embodiments also include isotopically-labeled compounds of Formula I, wherein one or more atoms is replaced by an atom having the same atomic number, but an atomic mass or mass number different from the atomic mass or mass number usually found in nature. Isotopically-labeled compounds of Formula I can generally be prepared by conventional techniques known to those skilled in the art or by processes analogous to those described herein, using an appropriate isotopically-labeled reagent in place of the non-labeled reagent otherwise employed.

Compounds of the disclosed embodiments intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the disclosed embodiments or in combination with one or more other drugs (or as any combination thereof). Generally, they will be administered as a formulation in association with one or more pharmaceutically acceptable excipients. The term 'excipient' is used herein to describe any ingredient other than the compound(s) of the disclosed embodiments. The choice of excipient will to a large extent depend on factors such as the particular mode of administration, the effect of the excipient on solubility and stability, and the nature of the dosage form.

Pharmaceutical compositions suitable for the delivery of compounds of the disclosed embodiments and methods for their preparation will be readily apparent to those skilled in the art. Such compositions and methods for their preparation may be found, for example, in Remington's Pharmaceutical Sciences, 19th Edition (Mack Publishing Company, 1995).

The compounds of the disclosed embodiments may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the disclosed embodiments may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula I, a film-forming polymer, a binder, a solvent, a humectant, a plasticiser, a stabiliser or emulsifier, a viscosity-modifying agent and a solvent. Some components of the formulation may perform more than one function.

The compound of formula I may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula I may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the disclosed embodiments are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations including delayed-, sustained-, pulsed-, controlled-, targeted and programmed release are of particular interest. Suitable modified release formulations for the purposes of the disclosed embodiments are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

The compounds of the disclosed embodiments may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Capsules (made, for example, from gelatin or hydroxypropylmethylcellulose), blisters and cartridges for use in an inhaler or insufflator may be formulated to contain a powder mix of the compound of the disclosed embodiments, a suitable powder base such as lactose or starch and a performance modifier such as 1-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

The compounds of the disclosed embodiments can also be formulated as Drug-cyclodextrin complexes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Since the aspects of the disclosed embodiments may relate to the treatment of the disease/conditions described herein with a combination of active ingredients which may be administered separately, they also relate to combining separate pharmaceutical compositions in kit form. The kit comprises two separate pharmaceutical compositions: a compound of Formula I or a salt of such compound and a second compound as described above. The kit comprises means for containing the separate compositions such as a container, a divided bottle or a divided foil packet. Typically the kit comprises directions for the administration of the separate components.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Summary of Pharmacokinetic Parameters for Compounds of Formula I

Binding to Opioid Receptors (Binding Assay)

Membrane preparations (from either rodent brain or from cells transfected with plasmids engineered to express an opioid receptor) are rapidly thawed and diluted in binding buffer (50 mM HEPES, 5 mM MgCl2, 1 mM CaCl2, 0.2% BSA, pH 7.4) to a concentration of 0.1 mg/mL. The radioligand and unlabeled compounds are diluted in binding buffer to achieve the desired final concentration in each well. The assays are performed in microtiter plates using 40 ul of binding buffer or unlabeled ligand, 10 ul of radioligand (final concentration of (3H)-DAMGO=2 nM), and 50 ul of diluted membranes with three wells per group. The plates are then incubated at room temperature for two hours. Unlabeled test compounds are added at one third-log increments with 5 log separation between highest and lowest concentrations. The binding incubation is terminated by the addition of 100 ul cold binding buffer to each well. The glass fiber filter plates are presoaked for 30-45 min with 0.33% polyethylenimine (PE)I buffer. The PEI solution is removed from the filter plate with a vacuum manifold (Millipore) and the filters washed with 200 ul priming buffer (50 mM HEPES, 0.5% BSA, pH 7.4) per well. The binding reaction is transferred to the filter plate and washed with 200 ul washing buffer (50 mM HEPES with 500 mM NaCl and 0.1% BSA, pH 7.4). The plate is dried and the filters removed using a cell harvester and punch assembly (MultiScreen HTS, Millipore) for analysis in a scintillation counter (Beckman Coulter, Fullerton, Calif.). For the competitive binding experiments with test compounds, the Ki value was calculated from the IC50 value by GraphPad Prism, using the equation of Cheng and Prusoff (1973).

Activation of Opioid Receptors (Functional Assay)

Opioid receptors belong to the seven transmembrane superfamily of heterotrimeric guanine nucleotide-binding protein-(G protein) coupled receptors, and are linked to the adenylyl cyclase-inhibitory G proteins Gi and Go (Carter and Medzihradsky, 1993). Thus a variety of in vitro assays may be used to establish agonist or antagonist properties of novel opioid receptor ligands, including GTP binding (using the non-hydrolyzable GTP analog GTPγS) and inhibition of cAMP accumulation.

The binding of the nonhydrolyzable GTP analog [$^{35}$S] GTPγS is often used to provide a measure of G protein activation by agonists (e.g., Lorenzen et al., 1993; Tian et al., 1994). Because G-protein activation is the first biochemical step after opioid receptor activation and is not limited by downstream effector systems, this assay provides a very direct measurement of efficacy, and the utility of this assay for determining the relative efficacies of mu opioid agonists in vitro has been demonstrated (Traynor and Nahorski 1995; Emmerson et al, 1996). The correlation between the intrinsic activity of a drug in this assay and its efficacy in vivo makes it an appropriate system for measuring the relative efficacies of opioid receptor agonists.

Cell culture. C6(m) rat glioma cells (which lack endogenous opioid receptors) which had been stably transfected with an opioid receptor-expressing plasmid (Emmerson et al., 1996) are grown under 5% CO2 in Dulbecco's modified Eagle's medium containing 10% fetal bovine serum. Stock flasks are maintained in the presence of 1 mg/ml Geneticin to select for the presence of the transfected plasmid, which codes for both the opioid receptor and antibiotic resistance. Cells used for experiments are split from the stock flasks and grown to confluence in the absence of Geneticin.

Membrane preparation. Cells are rinsed twice with ice-cold phosphate-buffered saline (0.9% NaCl, 0.61 mM Na2HPO4, 0.38 mM KH2PO4, pH 7.4) and detached from dishes by incubation with lifting buffer (5.6 mM glucose, 5 mM KCl, 5 mM HEPES, 137 mM NaCl, 1 mM EGTA, pH 7.4). The cells are then pelleted by centrifugation, resuspended in ice-cold lysis buffer (0.2 mM MgSO4, 0.38 mM KH2PO4, 0.61 mM Na2HPO4, pH 7.4) and homogenized using a glass-glass Dounce homogenizer. Membranes are then isolated by centrifugation for 20 min at 20,000×g at 4° C. The resulting membrane pellets are resuspended in 50 mM Tris buffer (pH 7.4) and stored at −80° C. in 1-ml aliquots (approximately 1 mg protein/ml).

Protein determination. Protein concentration in membrane samples is determined by the method of Lowry et al. (1951), using bovine serum albumin as a standard. Samples are solubilized by incubation at room temperature in 0.5N NaOH for 30 min before protein determination.

[35S]GTPγS binding assay. Varying concentrations of ligand are preincubated with membranes (15 mg membrane protein/tube) for 2 hr at 25° C. in binding cocktail [30 mM GDP, 1 mM dithiothreitol, I mM EDTA, 5 mM MgCl2, 100 mM NaCl and 47 mM Tris (pH 7.4)] in a 200 ml final assay volume. Experiments are initiated by the addition of [35S] GTPγS (final concentration 40 pM), which is added in a volume of 10 ul H$_2$O, to minimize any dilution of ligand and other reagents. After 1 min the reaction is terminated by the addition of 2 ml ice-cold washing buffer (50 mM Tris, 5 mM MgCl2, 100 mM NaCl) and the contents of the tubes are rapidly filtered through glass fiber filters (Schleicher & Schuell no. 32, Keene, N.H.). The tubes and filters are then rinsed with 2 ml washing buffer an additional three times. Filters are placed in scintillation vials containing 400 ml ethanol and 4-ml scintillation cocktail for liquid scintillation counting. Nonspecific counts are determined from tubes which contained 100 nM unlabeled GTPγS.

Inhibition of cAMP Accumulation. In this assay, cells expressing opioid receptors (either endogenous or recombinant) are first treated with agents which elevate intracellular cAMP (eg, PGE1 or forskolin) after which test compounds are added to the culture medium and intracellular cAMP is measured by radioimmunoassay or ELISA (Yu et al, 1990, Blake, 1997). Specifically, cell monolayers are treated for approximately 30 min at 37° C. with culture medium containing 0.5 mM isobutylmethylxanthine. After treatment, the medium is replaced with medium containing test compound at several different concentrations (eg, 10-11 to 10-6 M) and incubated at 37° C. for 5 min. The medium is then aspirated, and 1 ml of 0.1N HCl was added; the cells are sonicated and the monolayers were frozen at −20° C. For determination of the cAMP content of each well, the monolayers are thawed, placed on ice, sonicated, and the intracellular cAMP levels measured by radioimmunoassay (Amersham plc, Buckinghamshire, UK). Data obtained from the dose-response curves is then analyzed by nonlinear regression (using GraphPad Prism 2.01 from GraphPad Software, Inc., San Diego, Calif.) to calculate agonist potency.

In Vivo Measurement of Analgesic Activity and Opioid Side Effects

Determination of analgesic activity is well known to those skilled in the art. Several methods recognized as characterizing activity are listed below.

Tail Flick Test.

The method, which detects analgesic activity, follows that described by D'Amour and Smith (1941). Briefly, a mouse's tail is heated by means of a thermal light source or by immersion in hot water. The latency before the animal withdraws its tail is measured (with a maximum time of exposure to heat of 15 seconds). Opioids are well known to significantly increase the latency to tail withdrawal in this assay. In this assay the parent opioid is used as the reference substance (eg, hydrocodone, oxycodone etc), and the dose and pretreatment time for a test agent (eg, a quaternary ammonium derivative) is dependent on the route of administration of the test agent (could be oral, subcutaneous, intraperitoneal or intrathecal).

Formalin Test

As described by Shibata et al (1989), 25 ul of 0.5% sterile formalin was administered into the right hind paw of a mouse, which elicits a characteristic, biphasic behavioral response. Each animal was then returned to the chamber and pain response was recorded for a period of 30 min. The summation of time (in seconds) spent licking and biting the injected paw during each 5 minute block was measured as an indicator of pain response. Test agents are administered at various times and doses prior to formalin injection via oral, subcutaneous, intraperitoneal or intrathecal routes. In this assay, the parent opioid is used as the reference substance (eg, hydrocodone, oxycodone etc), and the dose and pretreatment time for a test agent (eg, a quaternary ammonium derivative of the parent opioid) to exert analgesic activity is calculated relative to the parent opioid.

An important side effect of chronic opioid use is constipation. The method below describes how a compound of the disclosed embodiments can be demonstrated to exhibit reduced activity on gastrointestinal motility relative to the parent opioid.

Gastrointestinal (GI) Transit.

For measurements of GI transit (Green, 1959), rats were fed by oral gavage with 2 ml of a test meal consisting of 10% vegetable charcoal in water. Five minutes afterwards animals were euthanized, their small intestine was removed, its length was measured (from the pyloric sphincter to the ileocecal junction) and the distance traveled by the test meal was recorded as a percentage of the total length (percentage of GI transit). The effect of test agents (eg, quaternary ammonium derivative of parent opioid) on GI motility is measured relative to the parent opioid as a reference, with either substance being administered at various times prior to oral gavage with the charcoal meal.

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed below are only illustrative of the invention. It should be understood that various modifications can be made without departing from the spirit of the invention. Accordingly, the invention is limited only by the claims.

REFERENCES

Alt, A et al, (1998) Stimulation of guanosine-5'-O-(3-[35S]thio)triphosphate binding by endogenous opioids acting at a cloned mu receptor. J Pharmacol Exp Ther. 286(1):282-8.

Blake A D, Bot G, Freeman J C, Reisine T. (1997) Differential opioid agonist regulation of the mouse mu opioid receptor. J Biol Chem. 272(2):782-90.

Carter, B. D. and Medzihradsky, F. (1993) Go mediates the coupling of the mu opioid receptor to adenylyl cyclase in cloned neural cells and brain. Proc Natl Acad Sci, 90:4062-4066.

Cheng, Y. and Prusoff, W. H., (1973) Relationship between the inhibition constant (Ki) and the concentration of inhibitor which causes 50 percent inhibition (1050) of an enzymatic reaction. Biochem. Pharmacol. 22, 3099-3108.

Emmerson P J, Clark M J, Mansour A, Akil H, Woods J H and Medzihradsky F (1996) Characterization of opioid agonist efficacy in a C6 glioma cell line expressing the m opioid receptor. J Pharmacol Exp Ther 278:1121-1127.

Lorenzen A, et al, (1993) Measurement of guanine nucleotide-binding protein activation by A1 adenosine receptor agonists in bovine brain membranes: Stimulation of guanosine-59-O-(3-[35S]-triphosphate binding. Mol Pharmacol 44:115-123.

Lowry O H, Rosebrough N J, Farr A L, Randall R J (1951). Protein measurement with the Folin phenol reagent. J. Biol. Chem. 193 (1): 265-75.

Tian W-N, Duzic E, Lanier S M and Deth R C (1994) Determinants of a2-adrenergic receptor activation of G proteins: Evidence for a precoupled receptor/G protein state. Mol Pharmacol 45:524-531.

Traynor J R and Nahorski S R (1995) Modulation by mu-opioid agonists of guanosine-5'-O-(3-[35S]thio) triphosphate binding to membranes from human neuroblastoma SH—SY5Y cells. Mol Pharmacol 47:848-854.

Vallejo R, et al (2011) Pharmacology of opioids in the treatment of chronic pain syndromes. Pain Physician. 14(4):E343-60.

Yu V C, Eiger S, Duan D S, Lameh J, Sadée W. (1990) Regulation of cyclic AMP by the mu-opioid receptor in human neuroblastoma SH—SY5Y cells. J Neurochem. 55(4):1390-6.

The invention claimed is:

1. A compound of the formula

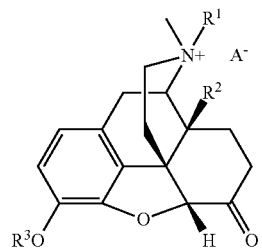

wherein $R^1$ is $CHR^4O(C=O)R^6$;
$R^2$ is OH;
$R^3$ is $CH_3$;
$R^4$ is H;
$R^5$ is alkyl selected from the group consisting of methyl, ethyl, propyl, butyl, isopropyl, diethylmethyl, isobutyl, sec-butyl, and t-butyl;
$R^6$ is $R^5$; and
A is an anion selected from the group consisting of: $Br^-$, $Cl^-$, $I^-$, $R^7CO_2^-$, $H_2PO_4^-$, $NO_3^-$, Etodolate, Mefenamate, Urosodeoxycholate and $R^6SO_3$.

2. A composition according to claim 1 wherein said composition is in tablet, capsule, oral solution, or oral suspension dosage form.

3. The compound
((3R,4aR,7aR,12bS)-9-methoxy-3-methyl-7-oxo-1,2,4,4a,5,6,7,7a-octahydro-3H-3λ$^4$-4,12-methanobenzofuro[3,2-e]isoquinolin-3-yl)methyl acetate;
((3S,4aR,7aR,12bS)-9-methoxy-3-methyl-7-oxo-1,2,4,4a,5,6,7,7a-octahydro-3H-3l$^4$-4,12-methanobenzofuro[3,2-e]isoquinolin-3-yl)methyl acetate;
ethyl (((3R,4aR,7aR,12bS)-9-methoxy-3-methyl-7-oxo-1,2,4,4a,5,6,7,7a-octahydro-3H-3l$^4$-4,12-methanobenzofuro[3,2-e]isoquinolin-3-yl)methyl) carbonate;
ethyl (((3S,4aR,7aR,12bS)-9-methoxy-3-methyl-7-oxo-1,2,4,4a,5,6,7,7a-octahydro-3H-3l$^4$-4,12-methanobenzofuro[3,2-e]isoquinolin-3-yl)methyl) carbonate;
((3R,4aR,7aR,12bS)-9-methoxy-3-methyl-7-oxo-1,2,4,4a,5,6,7,7a-octahydro-3H-3λ$^4$-4,12-methanobenzofuro[3,2-e]isoquinolin-3-yl)methyl pivalate;
((3S,4aR,7aR,12bS)-9-methoxy-3-methyl-7-oxo-1,2,4,4a,5,6,7,7a-octahydro-3H-3λ$^4$-4,12-methanobenzofuro[3,2-e]isoquinolin-3-yl)methyl pivalate;
(3S,4aR,7aR,12bS)-9-methoxy-3-methyl-3-((5-methyl-2-oxo-1,3-dioxol-4-yl)methyl)-2,3,4,4a,5,6-hexahydro-1H-3λ$^4$-4,12-methanobenzofuro[3,2-e]isoquinolin-7(7aH)-one;
(3R,4aR,7aR,12bS)-9-methoxy-3-methyl-3-((5-methyl-2-oxo-1,3-dioxol-4-yl)methyl)-2,3,4,4a,5,6-hexahydro-1H-3λ$^4$-4,12-methanobenzofuro[3,2-e]isoquinolin-7(7aH)-one;
(3R,4aR,7aR,12bS)-3-(((((cyclohexyloxy)carbonyl)oxy)methyl)-9-methoxy-3-methyl-7-oxo-2,3,4,4a,5,6,7,7a-octahydro-1H-4,12-methanobenzofuro[3,2-e]isoquinolin-3-ium;
cyclohexyl (((3S,4aR,7aR,12bS)-9-methoxy-3-methyl-7-oxo-1,2,4,4a,5,6,7,7a-octahydro-3H-3λ$^4$-4,12-methanobenzofuro[3,2-e]isoquinolin-3-yl)methyl) carbonate;
(3R,4aR,7aR,12bS)-9-hydroxy-3-methyl-7-oxo-3-((pivaloyloxy)methyl)-2,3,4,4a,5,6,7,7a-octahydro-1H-4,12-methanobenzofuro[3,2-e]isoquinolin-3-ium;

((3S,4aR,7aR,12bS)-9-hydroxy-3-methyl-7-oxo-1,2,4,4a,5,6,7,7a-octahydro-3H-3λ$^4$-4,12-methanobenzofuro[3,2-e]isoquinolin-3-yl)methyl pivalate;

(3R,4aS,7aR,12bS)-4a,9-dihydroxy-3-methyl-7-oxo-3-((pivaloyloxy)methyl)-2,3,4,4a,5,6,7,7a-octahydro-1H-4,12-methanobenzofuro[3,2-e]isoquinolin-3-ium;

((3S,4aS,7aR,12bS)-4a,9-dihydroxy-3-methyl-7-oxo-1,2,4,4a,5,6,7,7a-octahydro-3H-3λ$^4$-4,12-methanobenzofuro[3,2-e]isoquinolin-3-yl)methyl pivalate;

(3R,4aS,7aR,12bS)-4a-hydroxy-9-methoxy-3-methyl-7-oxo-3-((pivaloyloxy)methyl)-2,3,4,4a,5,6,7,7a-octahydro-1H-4,12-methanobenzofuro[3,2-e]isoquinolin-3-ium; or ((3S,4aS,7aR,12bS)-4a-hydroxy-9-methoxy-3-methyl-7-oxo-1,2,4,4a,5,6,7,7a-octahydro-3H-3λ$^4$-4,12-methanobenzofuro[3,2-e]isoquinolin-3-yl)methyl pivalate.

\* \* \* \* \*